United States Patent
Rodriguez

[11] Patent Number: 5,875,780
[45] Date of Patent: Mar. 2, 1999

[54] UNI-BODY SURGICAL DRAPE

[75] Inventor: Ruben Rodriguez, El Paso, Tex.

[73] Assignee: RCM Converters, Inc., El Paso, Tex.

[21] Appl. No.: 609,854

[22] Filed: Mar. 1, 1996

[51] Int. Cl.⁶ .................................................. A61B 19/00
[52] U.S. Cl. .......................................... 128/849; 128/853
[58] Field of Search .................................... 128/849–856

[56] References Cited

U.S. PATENT DOCUMENTS

| | | |
|---|---|---|
| 3,856,005 | 12/1974 | Sislian . |
| 3,856,006 | 12/1974 | Krzewinski . |
| 3,862,632 | 1/1975 | Hinsch ...................................... 128/853 |
| 4,489,720 | 12/1984 | Morris et al. . |
| 4,569,341 | 2/1986 | Morris . |
| 4,574,796 | 3/1986 | Lundstrom et al. . |
| 4,586,498 | 5/1986 | Morris . |
| 4,976,274 | 12/1990 | Hanssen . |
| 5,388,593 | 2/1995 | Thomalla . |
| 5,413,118 | 5/1995 | Thompson ............................... 128/853 |
| 5,452,729 | 9/1995 | Bergstaken et al. . |
| 5,464,024 | 11/1995 | Mills ........................................ 128/853 |
| 5,640,975 | 6/1997 | Diao ........................................ 128/853 |

*Primary Examiner*—Michael A. Brown
*Attorney, Agent, or Firm*—R. Wayne Pritchard

[57] ABSTRACT

A one piece "T" shaped surgical drape of uni-body construction is disclosed which provides for a drape covers which extends vertically from and contoured to the armboard and legboard covers. A bottom sheet portion can be added to the surgical drape to cover the leg area of a patient.

21 Claims, 3 Drawing Sheets

UNI-BODY SURGICAL DRAPE

FIELD OF THE INVENTION

The present invention relates to disposable surgical drapes and particularly to surgical drapes for use in all types of surgical procedures including, but not limited to, cardiovascular, laparotomy, OBGYN, head and neck, and orthopedic.

BACKGROUND OF THE INVENTION

Surgical drapes are utilized by operating room personnel during surgery in order to minimize, if not eliminate, bacterial as well as other forms of contamination from the actual surgical site. The "surgical drape" of prior art in general, consists of multiple pieces of fabric attached in a particular manner as to form a block "T" shape, large enough to cover the patient's body as well as, in some cases, the operating room table which includes the armboard and legboard surfaces. Generally, the drape includes a fenestration or hole through which the actual surgery is conducted. The area immediately adjacent to the fenestration is commonly referred to as the "critical zone" since this is the area where the physician will be performing the actual surgical procedures. Surgical drapes are customarily used during all types of surgical procedures, including, but not limited to, laparotomy, child birth, and all forms of cardiovascular care.

Examples of "T" shaped surgical drapes are disclosed in U.S. Pat. Nos. 4,586,498; 4,489,720 and 3,856,006. U.S. Pat. No. 3,856,006 discloses a "T" shaped surgical drape consisting of at least two pieces of fabric fastened together in such a fashion as to form the wing or armboard extensions as well as a torso section, including the legboard extensions. The two pieces of fabric are attached together in such a manner as to permit the armboard covers to cover the patient and to hang substantially vertically downward over the edge of the operating room table when the drape is in use. The seam between the pieces of fabric extends laterally across the drape through the critical zone.

U.S. Pat. No. 4,489,720 discloses a "T" shaped surgical drape utilized for cesarean section. As with U.S. Pat. No. 3,856,006, U.S. Pat. No. 4,489,720 discloses multiple pieces of fabric fastened together into a block "T" shape allowing coverage of both the torso as well as the arms of a patient. There is material overlap between the pieces of fabric and the seam between such pieces of fabric extends laterally through the critical zone and adjacent to the fenestration. U.S. Pat. No. 4,489,720 does not teach nor disclose any coverage for the armboard or legboard extension nor does such patent reveal any mechanism which would allow a surgical drape to both cover a patient and extend vertically downward from and contoured to the armboard and legboard extensions.

U.S. Pat. No. 4,586,498 discloses a "T" shaped surgical drape fabricated from multiple pieces of material through the time-consuming task of, in general, 1) cutting the drape; 2) folding the cut portions of the drape at 45° angles; and, 3) refolding the drape. According to U.S. Pat. No. 4,586,498, the result of the folding sequence provides a single edge which may be attached to the top edge of the main portion of the drape by adhesive. The attachment sequence of U.S. Pat. No. 4,586,498 apparently permits the armboard and legboard covers to drape vertically from such covers.

As can clearly be appreciated by those skilled in the art, the wish list of ingredients for the ideal "T" shaped surgical drape is that such drape would be 1) constructed from inexpensive fabric; 2) easy to manufacture; 3) utilizes a minimum amount of fabric; 4) prevents contamination of the surgical site and 5) permits the drape to both cover the patient and extend vertically from and contoured to the armboard and legboard covers. None of the prior art discloses such ingredients. The overlap of material created by the methods employed in the prior art of forming the wing or arm portion results in material waste. The method of fastening the fabric in the prior art results in a seam extending through the critical zone creating the possibility of contamination in spots where the seam is imperfect. The method of forming the arm portions in the prior art is both time consuming as well as cumbersome.

SUMMARY OF THE INVENTION

The present invention incorporates all of the ingredients necessary for the ideal surgical drape. The present invention provides a one piece "T" shaped uni-body surgical drape for use on an operating table to cover during surgery both a patient as well as the armboard and legboard extension. The surgical drape of the present invention utilizes a fabric which is disposable, lightweight, and inexpensive as well as capable of repelling water and other liquids commonly associated with surgical procedures. In order to employ the use of heat to form the seams necessary in the present invention, the fabric would also have to have thermal properties.

The surgical drape of the present invention is one piece of fabric formed in the general shape of a block "T". To allow the "T" shaped or arm portions of the drape to hang substantially vertically downward from and contoured to the armboard and legboard covers when the drape is in use, a series of cuts and folds are made to a rectangular sheet of material. The uni-body design of the present invention permits the use of automated equipment during the manufacturing process.

The uni-body surgical drape is formed from a rectangular sheet of material having a top edge, two side edges and a bottom edge. A first and second cut is made to the rectangular sheet of material perpendicular to the bottom edge at a distance of between 6 and 23.5 inches inward from the side edges, parallel to such edges for a distance of between 47 and 52.5 inches.

A third and fourth cut is made from and perpendicular to the end of the first and second cut outward to the side edges. Beginning at the end of the first and second cut, a fifth and sixth cut is made parallel to the side edges for a distance of between 12 and 15 inches. A seventh and eighth cut is made beginning at the top edge at a distance of between 1 and 6 inches inward from the side edges and extending parallel to the side edges for a distance of between 38.5 and 44 inches. A ninth and tenth cut is made from and perpendicular to the end of the seventh and eighth cut outward to the side edges. An eleventh and twelfth cut is made parallel to the side edges beginning 1–3 inches perpendicular to the end of the seventh and eighth cuts to the third and fourth cuts.

Beginning at the end of the seventh and eighth cut and extending perpendicular to such cuts inward into the rectangular sheet of material for a distance of between 27 and 30 inches, a thirteenth and fourteenth cut is made.

The rectangular sheet of material is then folded from the side edges along the fifth and sixth cuts until the side edges come into contact with the rectangular sheet of material forming a cover flap. The cover flap is then attached to the rectangular sheet of material along its top edge, leaving between one and three inches of unattached edges towards the center of the rectangular sheet of material. The cover flap is then folded from the point innermost and uppermost, upward towards the top edge until the cover flap aligns horizontally with the edges of the thirteenth and fourteenth cut. The cover flap is then attached to the rectangular sheet of material along the thirteenth and fourteenth cuts.

A fifteenth and sixteenth cut is then made beginning at the end of the first and second cut inward into the cover flap up to but not through the attachment along the thirteenth and fourteenth cuts.

An additional embodiment of the present invention provides a drape with integral bottom sheet. The bottom sheet portion is attached to the main portion of the surgical drape utilizing any suitable means such as sewing, gluing or heat sealing.

BRIEF DESCRIPTION OF THE DRAWINGS

The surgical drape of the present invention can be more clearly understood through reference to the following drawings in which.

DETAILED DESCRIPTION OF THE INVENTION

Figure 1:
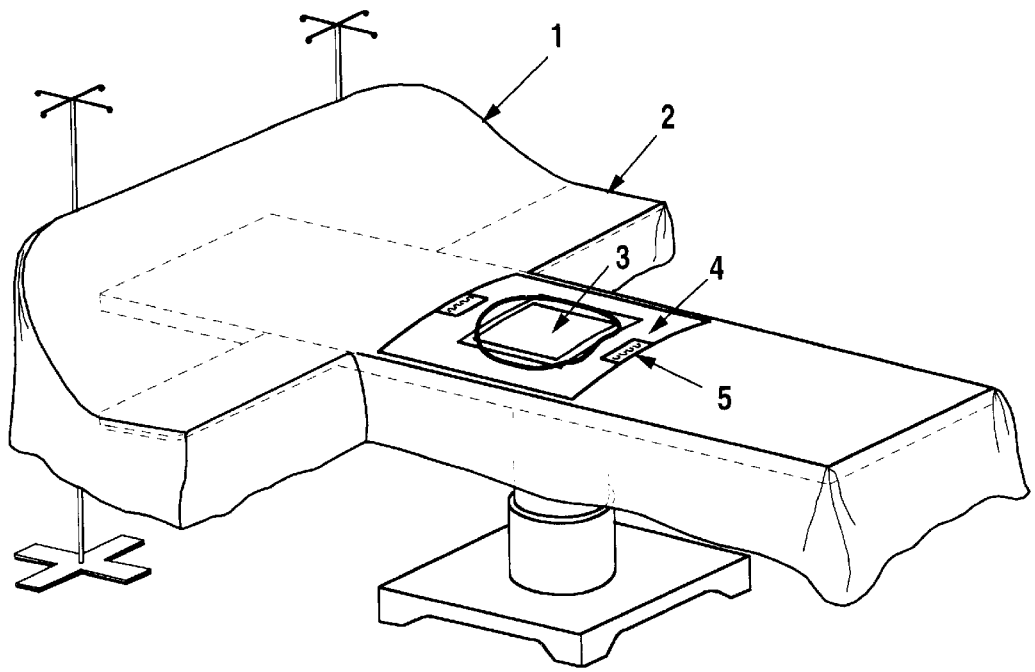
FIG. 1 is an isometric illustration of the uni-body surgical drape of the present invention in place on an operating room table.

FIG. 1 is an illustration of the surgical drape of the present invention as such drape would appear when placed upon an operating room table showing the anesthesia screen 1 and armboard covers 2.

Figure 2:
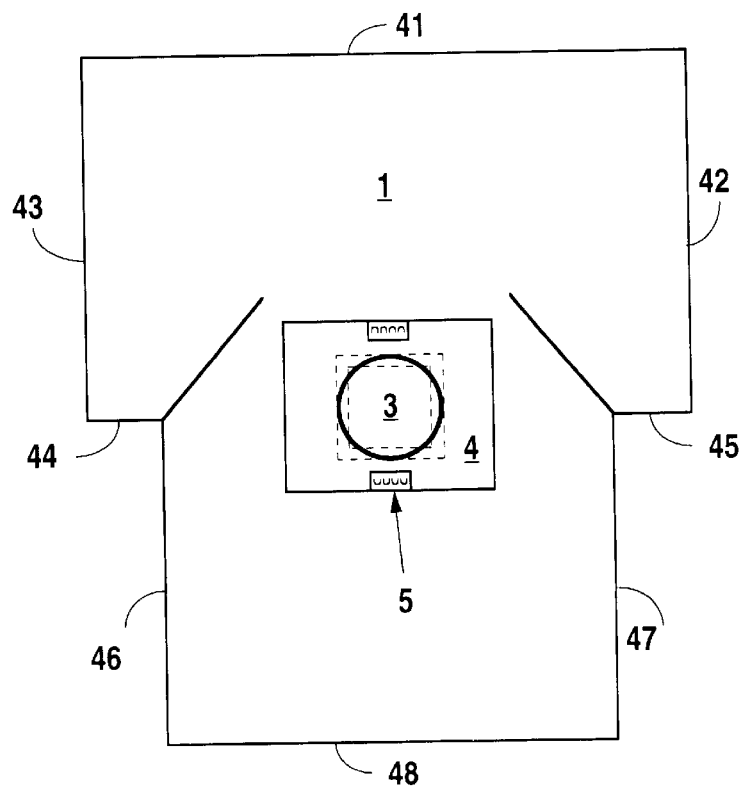
FIG. 2 is a top plan view of the uni-body surgical drape of the present invention.

FIG. 2 depicts a top plan view of the surgical drape of the present invention illustrating the top edge 41, the two opposing edges 42, 43, the two side edges 44, 45, two opposing indented edges 46, 47, and the bottom edge 48. Also shown in FIG. 2 is one possible site for the fenestration 3 as well as the reinforcing area 4 and instrument pad 5. The surgical drape is constructed of a lightweight, disposable, inexpensive synthetic or natural fabric capable of repelling water and other liquids commonly associated with surgical procedures. Although the present invention utilizes a fabric which possesses properties which allow all seams to be completed utilizing a heat sealing technique, other, more conventional techniques of completing seams such as gluing or sewing can be utilized.

Figure 3:
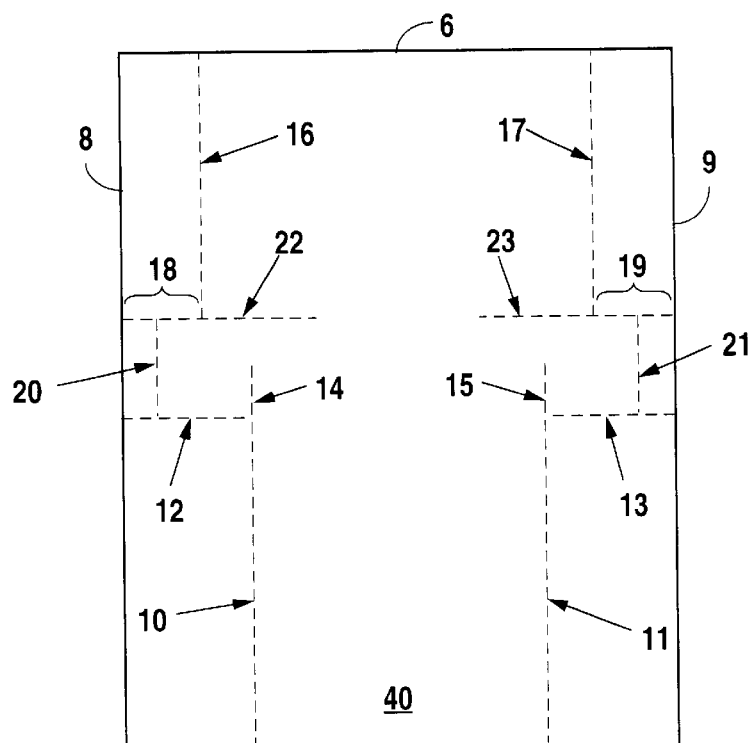
FIG. 3 is a top plan view of the rectangular sheet of material from which the uni-body surgical drape is made depicting the cut lines.

FIG. 3 depicts a rectangular sheet of material 40 from which the uni-body surgical drape is formed having a top edge 6, bottom edge 7 and two parallel side edges 8 and 9. Also depicted in FIG. 3 are the various cut lines needed to form the uni-body surgical drape. A first 10 and second 11; third 12 and fourth 13; fifth 14 and sixth 15; seventh 16 and eighth 17; ninth 18 and tenth 19; eleventh 20 and twelfth 21; and, thirteenth 22 and fourteenth 23 cut is shown.

Once the various cuts are made to the rectangular sheet of material 40, the uni-body surgical drape is ready for the various folds which will allow the drape to extend vertically from the arm board and leg board covers.

Figure 4:
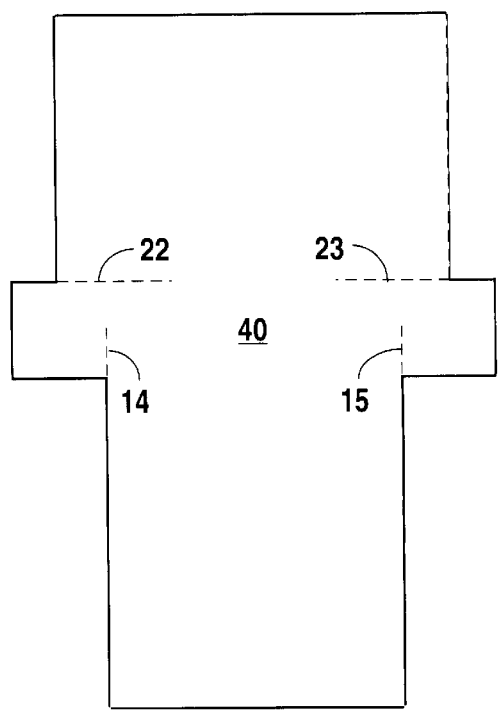
FIG. 4 is a top plan view of the uni-body surgical drape of the present invention depicting the first folding sequence.

FIG. 4 depicts the uni-body surgical drape following the removal of the unused portions of the rectangular sheet of material 40 and further illustrating the fifth 14, sixth 15, thirteenth 22 and fourteenth 23 cuts.

Figure 5:
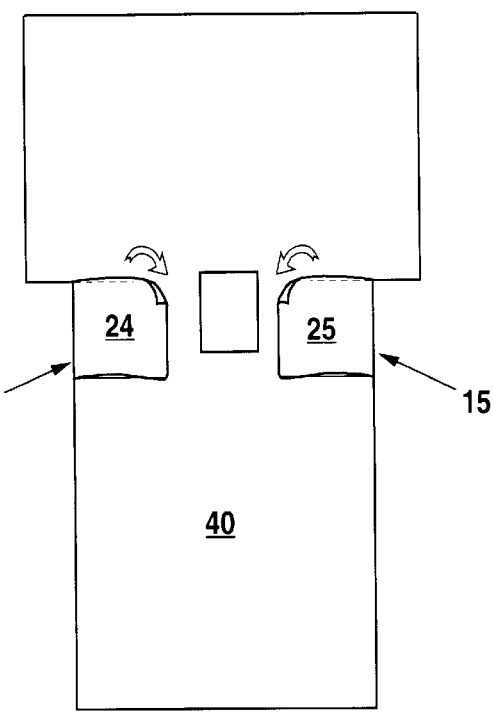
FIG. 5 shows a top plan illustration of the uni-body surgical drape of the present invention showing the first attachment.

FIG. 5 illustrates the first folding sequence from the side edges 8 and 9 inward along the fifth and sixth cuts 14 and 15 forming the cover flap 24 and 25.

Figure 6:
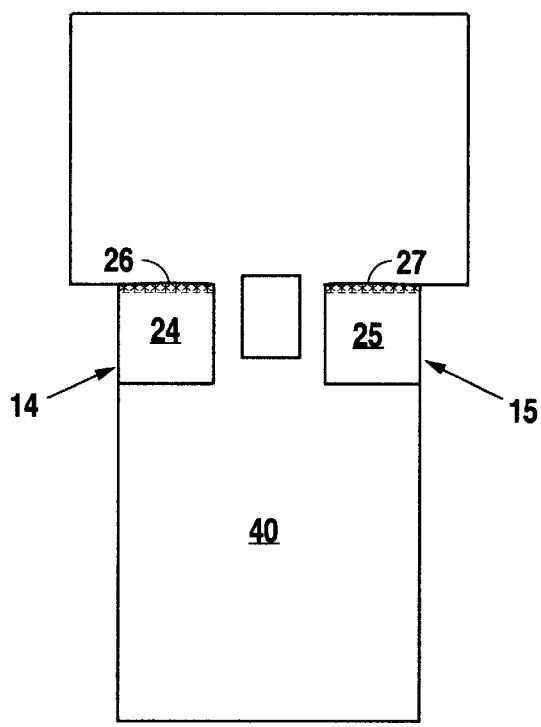
FIG. 6 shows a top plan view of the uni-body surgical drape of the present invention depicting the second folding sequence.

FIG. 6 illustrates the line of attachment along the upper edge 26 and 27 of the cover flap, 24 and 25.

Figure 7:
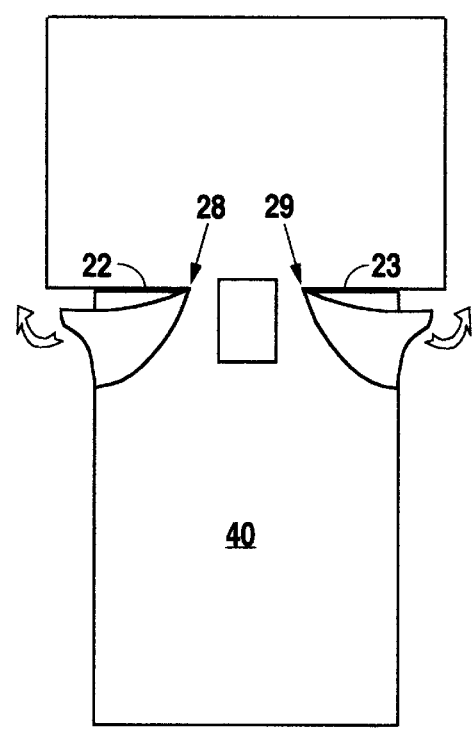
FIG. 7 shows a top plan view showing attachment of the cover flap.

FIG. 7 illustrates the second folding sequence from a point 28 and 29 uppermost and most inward of the cover flap 24 and 25 until the unattached edges of said cover flap aligns horizontally with the edges of thirteenth 22 and fourteenth 23 cuts.

Figure 8:
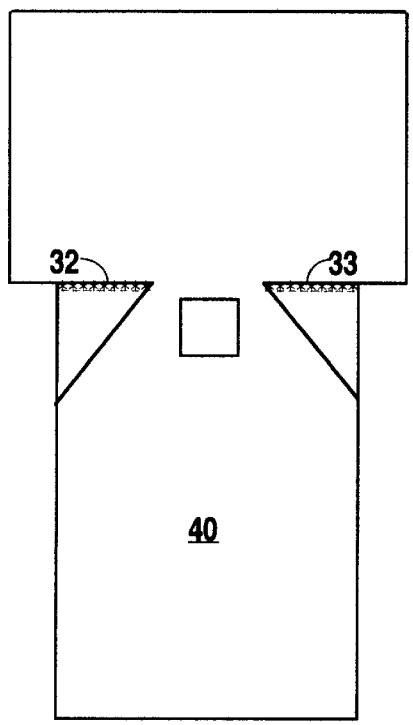
FIG. 8 shows a top plan view illustrating the final cut to the uni-body surgical drape.

FIG. 8 depicts the attachment of the cover flap 24 and 25 along its horizontal edge 32 and 33.

Figure 9:
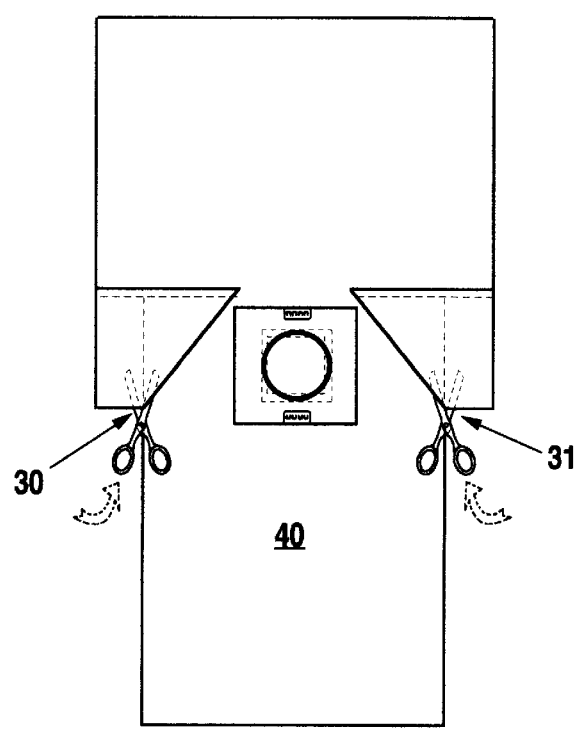
FIG. 9 shows a plan view of the final step in preparing the uni-body surgical drape.

FIG. 9 illustrates the fifteenth 30 and sixteenth 31 cuts up to but not through the attachment along the thirteenth 22 and fourteenth 23 cuts.

Once the initial fabrication as explained above is completed, additional features can be added to the surgical drape depending upon the requirements of the specific surgical procedure. A fenestration or opening 3 is shown in FIG. 2. The specific location of the fenestration 3 is dependent upon the type of surgical procedure employed. To provide additional protection in the surgical site, a reinforcing area 4 can be provided in the area surrounding the fenestration 3. Reinforced tabs for securing operating room equipment such as tubing as well as a reinforced instrument pad 5 can also be provided as shown in FIG. 2.

I claim:

1. A one piece surgical drape of uni-body construction for use on a patient during an operation comprising, when extended to cover said patient and the armboard and legboard surfaces upon which said patient is situated, a rectangular sheet of material having a top edge, bottom edge and two side edges wherein a first and second cut is made perpendicular to the bottom edge at a distance of between 6 and 23.5 inches inward from the side edges, parallel to such edges for a distance of between 47 and 52.5 inches; wherein a third and fourth cut is made from and perpendicular to the end of the first and second cut outward to the side edges; wherein a fifth and sixth cut is made beginning at the end of the first and second cut, parallel to the side edges for a distance of between 12 and 15 inches; wherein a seventh and eighth cut beginning at the top edge at a distance of between 1 and 6 inches inward from the side edges and extending parallel to the side edges for a distance of between 38.5 and 44 inches wherein a ninth and tenth cut from and perpendicular to the end of the seventh and eighth cuts outward to the side edges; wherein an eleventh and twelfth cut is made parallel to the side edges beginning 1–3 inches perpendicular to the end of the seventh and eighth cuts to the third and fourth cuts; wherein beginning at the end of the seventh and eighth cuts and extending perpendicular to such cuts inward and into the rectangular sheet of material for a distance of between 27 and 30 inches a thirteenth and fourteenth cut is made; wherein folds are made from the eleventh and twelfth cuts along the fifth and sixth cuts until the edges of the eleventh and twelfth cuts come into contact with the rectangular sheet of material forming a cover flap; wherein the top edge of the cover flap is attached to the rectangular sheet of material, leaving between 1–3 inches of unattached edge toward the center of the rectangular sheet of material; wherein the cover flap, from a point innermost and uppermost is folded upward until the cover flap aligns horizontally with the edges of the thirteenth and fourteenth cuts; wherein the cover flap is attached to the rectangular sheet of material along the thirteenth and fourteenth cuts; wherein a fifteenth and sixteenth cut is made beginning at the end of the first and second cuts inward into the cover flap up to, but not through the attachment along the thirteenth and fourteenth cuts.

2. The uni-body surgical drape of claim 1 wherein the length of the thirteenth and fourteenth cuts is 30 inches.

3. The uni-body surgical drape of claim 2 wherein the length of the fifth and sixth cuts is 15 inches.

4. The uni-body surgical drape of claim 1 wherein the length of the thirteenth and fourteenth cuts is 29 inches.

5. The uni-body surgical drape of claim 4 wherein the length of the fifth and sixth cuts is 14 inches.

6. The uni-body surgical drape of claim 1 wherein the length of the thirteenth and fourteenth cuts is 28 inches.

7. The uni-body surgical drape of claim 6 wherein the length of the fifth and sixth cuts is 13 inches.

8. The uni-body surgical drape of claim 1 wherein the length of the thirteenth and fourteenth cuts is 27 inches.

9. The uni-body surgical drape of claim 8 wherein the length of the fifth and sixth cuts is 12 inches.

10. The uni-body surgical drape of claim 1 wherein the top edge of the cover flap is attached to the rectangular sheet of material, leaving one inch of unattached edge towards the center of the rectangular sheet of material.

11. A method of forming a one piece surgical drape of uni-body construction in the general shape of a block "T" having a bottom edge, a top edge, two opposing extended edges and two opposing indented edges comprising the steps of:

(a) making a first and second cut made to a rectangular sheet of material perpendicular to the bottom edge at a distance of between 6 and 23.5 inches inward from the side edges, parallel to such edges for a distance of between 47 and 52.5 inches;

(b) making a third and fourth cut from and perpendicular to the end of the first and second cuts outward to side edges;

(c) making a fifth and sixth cut beginning at the end of the first and second cuts parallel to the side edges for a distance of between 12 and 15 inches;

(d) making a seventh and eighth cut beginning at the top edge at a distance of between 1 and 6 inches inward from the side edges and extending parallel to the side edges for a distance of between 38.5 and 44 inches;

(e) making a ninth and tenth cut from and perpendicular to the end of the seventh and eighth cuts outward to the side edges;

(f) making an eleventh and twelfth cut parallel to the side edges beginning 1–3 inches perpendicular to the end of the seventh and eighth cuts to the third and fourth cuts;

(g) beginning at the end of the seventh and eighth cuts and extending perpendicular to such cuts inward and into the rectangular sheet of material for a distance of between 27 and 30 inches, a thirteenth and fourteenth cut is made;

(h) folding from the eleventh and twelfth cuts along the fifth and sixth cuts until the edges of the eleventh and twelfth cuts come into contact with the rectangular sheet of material forming a cover flap;

(i) attaching the top edge of the cover flap to the rectangular sheet of material, leaving between 1 and 3 inches of unattached edges toward the center of the rectangular sheet of material;

(j) folding the cover flap from a point innermost and uppermost, upward until the cover flap aligns horizontally with the edges of the thirteenth and fourteenth cuts;

(k) attaching cover flap to the rectangular sheet of material along the thirteenth and fourteenth cuts;

(l) making a fifteenth and sixteenth cut beginning at the end of the first and second cuts inward into the cover flap up to, but not through, the attachment along the thirteenth and fourteenth cuts.

12. The method of claim 11 wherein the length of the thirteenth and fourteenth cut is 30 inches.

13. The method of claim 12 wherein the length of the fifth and sixth cut is 15 inches.

14. The method of claim 13 wherein the length of the thirteenth and fourteenth cut is 29 inches.

15. The method of claim 14 wherein the length of the fifth and sixth cut is 14 inches.

16. The method of claim 11 wherein the length of the thirteenth and fourteenth cut is 28 inches.

17. The method of claim 16 wherein the length of the fifth and sixth cut is 13 inches.

18. The method of claim 11 wherein the length of the thirteenth and fourteenth cut is 27 inches.

19. The method of claim 18 wherein the length of the fifth and sixth cut is 12 inches.

20. The method of claim 11 wherein the edge of the cover flap is attached to the rectangular sheet of material leaving one inch of unattached edge towards the center of the rectangular sheet of material.

21. The method of claim 11 wherein a means for attachment is any conventional means such as sewing, heat sealing or gluing.

* * * * *